US010755125B2

(12) United States Patent
Gupta et al.

(10) Patent No.: US 10,755,125 B2
(45) Date of Patent: Aug. 25, 2020

(54) FACE VIDEO BASED HEART RATE MONITORING USING PULSE SIGNAL MODELLING AND TRACKING

(71) Applicant: Tata Consultancy Services Limited, Mumbai (IN)

(72) Inventors: Puneet Gupta, Kolkata (IN); Brojeshwar Bhowmick, Kolkata (IN); Arpan Pal, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 321 days.

(21) Appl. No.: 15/900,788

(22) Filed: Feb. 20, 2018

(65) Prior Publication Data

US 2019/0171893 A1 Jun. 6, 2019

(30) Foreign Application Priority Data

Dec. 5, 2017 (IN) .............................. 201721043635

(51) Int. Cl.
*G06K 9/62* (2006.01)
*G06K 9/32* (2006.01)
(Continued)

(52) U.S. Cl.
CPC ........ *G06K 9/00885* (2013.01); *A61B 5/0077* (2013.01); *A61B 5/024* (2013.01); *A61B 5/02416* (2013.01); *A61B 5/7221* (2013.01); *A61B 5/7257* (2013.01); *A61B 5/7264* (2013.01); *G06K 9/0053* (2013.01);
(Continued)

(58) Field of Classification Search
None
See application file for complete search history.

(56) References Cited

U.S. PATENT DOCUMENTS 8,216,136 B2 * 7/2012 Addison .............. A61B 5/0205
600/301
2017/0367590 A1 * 12/2017 Sebe .................. G06K 9/00268

OTHER PUBLICATIONS

A. Schäfer, J. Vagedes, How accurate is pulse rate variability as an estimate of heart rate variability?: A review on studies comparing photoplethysmographic technology with an electrocardiogram, Intl Journal of Cardiology, vol. 166-1, pp. 15-29, ISSN 0167-5273,https://doi.org/10.1016/j.ijcard.2012.03.119.*

(Continued)

*Primary Examiner* — Tahmina N Ansari
(74) *Attorney, Agent, or Firm* — Finnegan, Henderson, Farabow, Garrett & Dunner LLP

(57) ABSTRACT

The present disclosure provides a non-invasive, inexpensive and unobtrusive system that enables heart rate (HR) monitoring by addressing the traditionally known issues with face video based systems due to respiration, facial expressions, out-of-plane movements, camera parameters and environmental factors. These issues are alleviated by filtering, pulse modelling and HR tracking. Quality measures are defined which incorporate out-of-plane movements to define the quality of each video frame unlike existing approaches which provide a single quality for the entire video. To handle out-of-plane movement, Fourier basis function is employed to reconstruct pulse signals at affected locations. Bayesian decision theory based method performs HR tracking using previous HR and quality estimates for improved HR monitoring.

9 Claims, 16 Drawing Sheets

(51) Int. Cl.
  G06K 9/00      (2006.01)
  G06K 9/03      (2006.01)
  A61B 5/024     (2006.01)
  A61B 5/00      (2006.01)
(52) U.S. Cl.
  CPC ..... *G06K 9/00261* (2013.01); *G06K 9/00268* (2013.01); *G06K 9/00523* (2013.01); *G06K 9/036* (2013.01); *G06K 9/3233* (2013.01); *G06K 9/6296* (2013.01); *G06K 2009/00939* (2013.01)

(56) References Cited

OTHER PUBLICATIONS

Sun, B. et al. (Dec. 2015). "Photophethysmography—Based Heart Rate Monitoring Using Asymmetric Least Squares Spectrum Subtraction and Bayesian Decision Theory," IEEE Sensors Journal, vol. 15, issue 12; pp. 7161-7168.

Wang, W. et al. (Mar. 2017). "Amplitude-selective filtering for remote-PPG," *Biomed Optics Express*, vol. 8, No. 3; 16 pages.

Sun, Y. (Jul. 2011). "Motion-compensated noncontact imaging photoplethysmography to monitor cardiorespiratory status during exercise," *Journal of Biomedical Optics*, vol. 16, No. 7; pp. 077010-1 to 077010-9.

Kumar, M. et al. (Apr. 2015). "DistancePPG: Robust non-contact vital signs monitoring using a camera," *Optical Society of America*, vol. 6, No. 5; 24 pages.

Xu, S. et al. (Apr. 2014). "Robust efficient estimation of heart rate pulse from video," *Biomedical Optics Express*, vol. 5, No. 4; pp. 1124-1135.

Stricker, R. et al. "Non-contact Video-based Pulse Rate Measurement on a Mobile Service Robot," *23rd IEEE International Symposium on Robot and Human Interactive Communication*, Edinburgh, UK, Aug. 25-29, 2014; pp. 1056-1062.

* cited by examiner

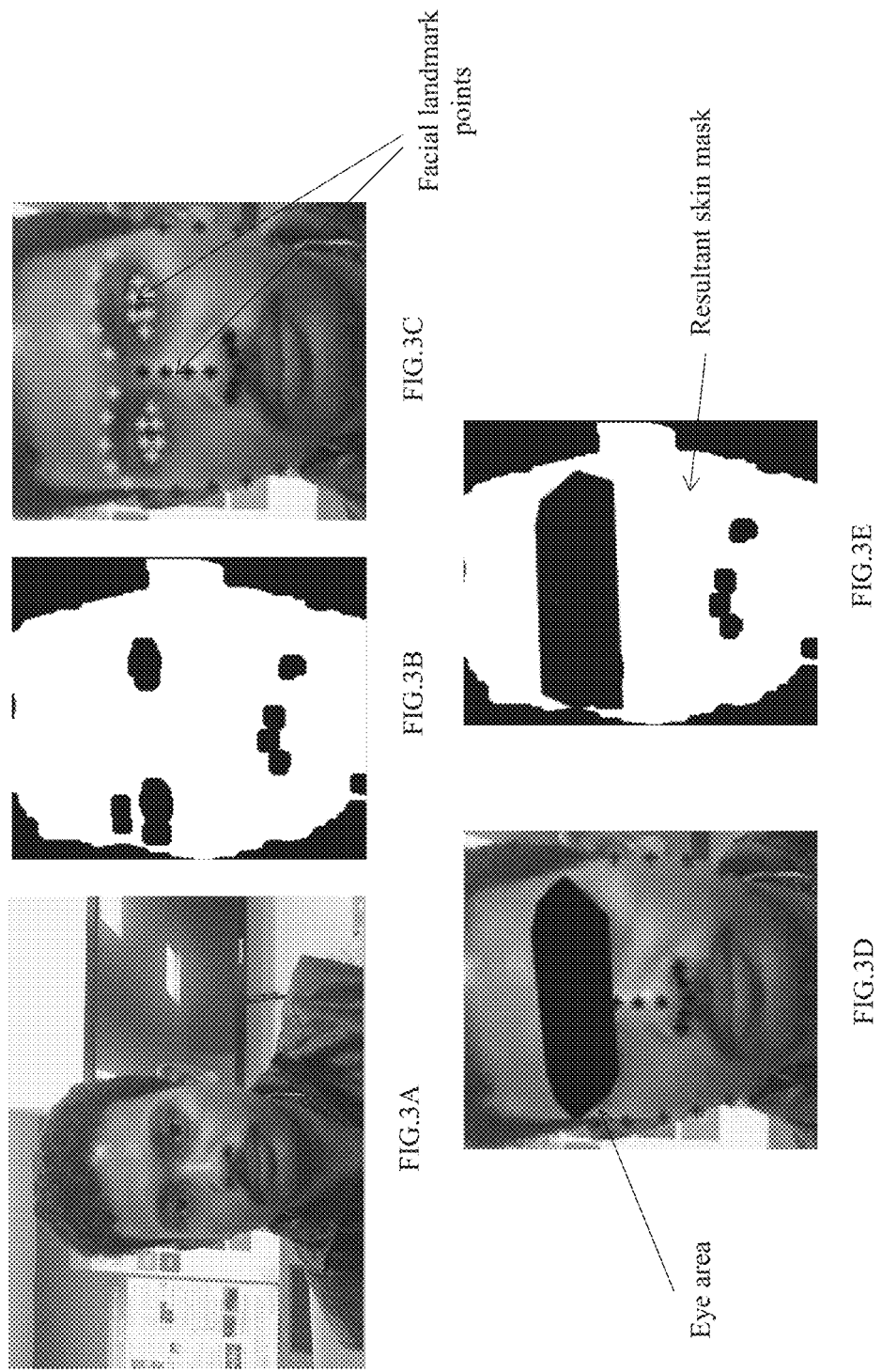

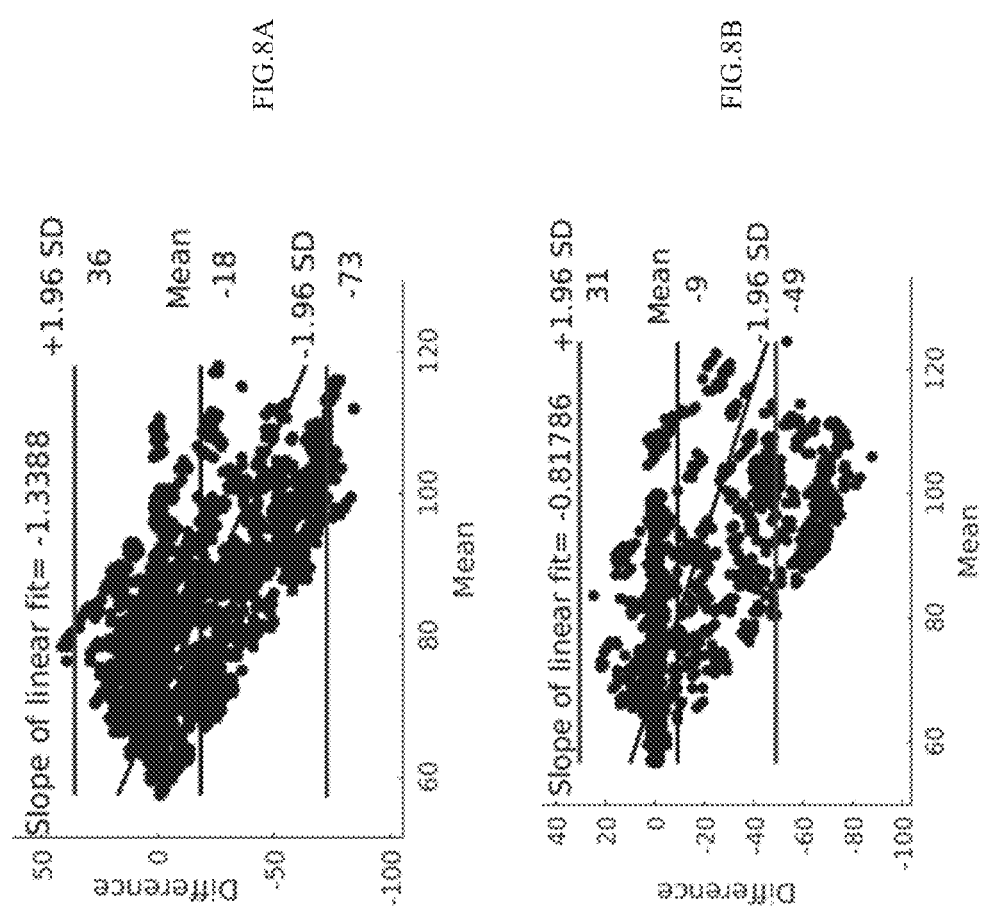

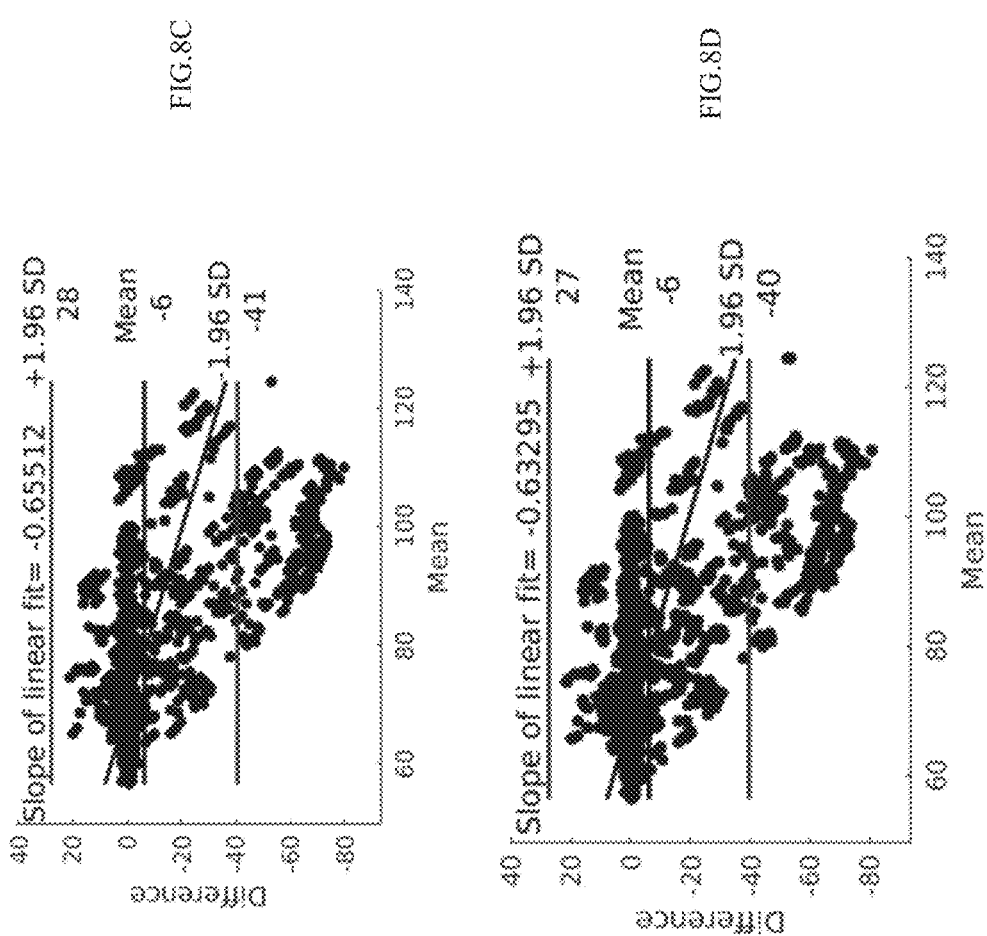

FACE VIDEO BASED HEART RATE MONITORING USING PULSE SIGNAL MODELLING AND TRACKING

PRIORITY CLAIM

This U.S. patent application claims priority under 35 U.S.C. § 119 to: Indian Patent Application No. 201721043635, filed on 5 Dec. 2017. The entire contents of the aforementioned application are incorporated herein by reference.

TECHNICAL FIELD

The disclosure herein generally relates to non-invasive physiological monitoring, and more particularly to face video based systems and methods for heart rate monitoring using pulse signal modelling and tracking.

BACKGROUND

Heart rate (HR) monitoring is required in many real-world applications like healthcare, psychology understanding, affective computing and biometrics. Using only face videos for HR estimation provides an advantage of creating a non-invasive, inexpensive and unobtrusive system. However, HR estimation using face videos can be erroneous due to respiration, facial expressions, out-of-plane movements, camera parameters (like focus change) and environmental factors.

SUMMARY

Embodiments of the present disclosure present technological improvements as solutions to one or more of the above-mentioned technical problems recognized by the inventors in conventional systems.

In an aspect, there is provided a processor implemented method comprising: extracting in real time, by a window extractor module, a plurality of non-overlapping windows from an input video with a detected face, wherein the non-overlapping windows correspond to time intervals of the input video, each of the time intervals containing an equal number of frames; analyzing, by a window analyzer module, each of the non-overlapping windows by: extracting a pulse signal from each of the non-overlapping windows; estimating a first quality measure as a quality of the pulse signal in each of the frames based on out-of-plane movement in a z direction, wherein the first quality measure has (f–1) values for f number of the frames; estimating a second quality measure based on peak signal to noise ratio (PSNR), wherein the second quality measure is a single value for the pulse signal; and post processing the pulse signal by reconstructing the pulse signal at the frames affected by the out-of-plane movements using the remaining frames to obtain modelled pulse signals; and tracking, by a heart rate (HR) tracker module, heart rate corresponding to the modelled pulse signal from each of the non-overlapping windows based on a Bayesian decision theory.

In another aspect, there is provided a system comprising: one or more processors; and one or more internal data storage devices operatively coupled to the one or more processors for storing instructions configured for execution by the one or more processors, the instructions being comprised in: a window extractor module configured to: extract in real time a plurality of non-overlapping windows from an input video with a detected face, wherein the non-overlapping windows correspond to time intervals of the input video, each of the time intervals containing an equal number of frames; a window analyzer module configured to: extract a pulse signal from each of the non-overlapping windows; estimate a first quality measure as a quality of the pulse signal in each of the frames based on out-of-plane movement in a z direction, wherein the first quality measure has (f–1) values for f number of the frames; estimate a second quality measure based on peak signal to noise ratio (PSNR), wherein the second quality measure is a single value for the pulse signal; and post process the pulse signal by reconstructing the pulse signal at the frames affected by the out-of-plane movements using the remaining frames to obtain modelled pulse signals; and a heart rate (HR) tracker module configured to: track heart rate corresponding to the modelled pulse signal from each of the non-overlapping windows based on a Bayesian decision theory In yet another aspect, there is provided a computer program product comprising a non-transitory computer readable medium having a computer readable program embodied therein, wherein the computer readable program, when executed on a computing device, causes the computing device to: extract in real time, a plurality of non-overlapping windows from an input video with a detected face, wherein the non-overlapping windows correspond to time intervals of the input video, each of the time intervals containing an equal number of frames; analyze each of the non-overlapping windows by: extracting a pulse signal from each of the non-overlapping windows; estimating a first quality measure as a quality of the pulse signal in each of the frames based on out-of-plane movement in a z direction, wherein the first quality measure has (f–1) values for f number of the frames; estimating a second quality measure based on peak signal to noise ratio (PSNR), wherein the second quality measure is a single value for the pulse signal; and post processing the pulse signal by reconstructing the pulse signal at the frames affected by the out-of-plane movements using the remaining frames to obtain modelled pulse signals; and track heart rate corresponding to the modelled pulse signal from each of the non-overlapping windows based on a Bayesian decision theory.

In an embodiment of the present disclosure, the step of extracting a pulse signal comprises: identifying a Region of Interest (ROI) corresponding to the detected face in each of the non-overlapping windows, wherein a face area associated with the detected face is divided into non-overlapping square blocks; performing frame registration between a previous frame and a current frame within each of the non-overlapping windows based on a pre-defined subset of facial landmark points to stabilize location of the ROI in presence of in-plane movement; extracting temporal signals from each of the non-overlapping square blocks of the ROI using Eulerian method, wherein the temporal signals correspond to motion or color variations in the detected face across time; and estimating the pulse signal from the extracted temporal signals using a kurtosis based optimization method.

In an embodiment of the present disclosure, the step of estimating a first quality measure as a quality of the pulse signal in each of the frames based on out-of-plane movement in a z direction comprises: calculating a deviation introduced by a change of location of pre-defined facial landmark points in the z direction, wherein the deviation is calculated between each pair of consecutive frames in each of the non-overlapping windows; estimating the first quality measure by utilizing the pre-defined facial landmark points having a largest deviation in the z direction by: normalizing the deviations in the pre-defined facial landmark points in the z direction to [0,1]; and estimating the first quality measure by subtracting the normalized deviations from 1 such that low and high deviations result in high and low values for the first quality measure respectively as $$\hat{q}_{(k-1)} = 1 - \left( \frac{d_{(k-1)} - \min(d)}{\max(d) - \min(d)} \right).$$

In an embodiment of the present disclosure, the post processing of the pulse signal comprises reconstructing the pulse signals at the frames affected by the out-of-plane movements using Fourier basis function based pulse signal modelling, the pulse signal modelling comprising: decomposing the pulse signal at the frames affected by the out-of-plane movements using the Fourier basis function; estimating pulse signal modelling parameters by using a weighted least square equation, wherein the pulse signal modelling parameters represent a contribution of the Fourier basis function and weights refer to the first quality measure, wherein solving the weighted least square equation is based on a pseudo inverse equation for minimizing an associated weighted error, and wherein the weighted error is based on the first quality measure and a reconstruction error at each frame; and obtaining the modelled pulse signal based on the estimated modelling parameters and the Fourier basis function.

In an embodiment of the present disclosure, the step of tracking the heart rate comprises: estimating the heart rate using the Bayesian decision theory by estimating a current heart rate corresponding to a current modelled pulse signal using previous heart rate of a preceding modelled pulse signal and the second quality measure associated with the current and the preceding modelled pulse signals; and analyzing a spectrum associated with the modelled pulse signal from each of the non-overlapping windows to identify frequency of a maximum amplitude corresponding to the heart rate thereof as an HR frequency.

In an embodiment of the present disclosure, wherein using the Bayesian decision theory comprises: determining a quality of the previous heart rate estimate by utilizing the second quality measure; calculating a Gaussian distribution of a prior information pertaining to a previously tracked HR and a likelihood function of a current modelled pulse signal by defining a measure of confidence in the previous heart rate estimate along with the determined quality of the previous heart rate estimate; estimating the prior information required for current heart rate estimation, wherein the prior information is estimated by finding a normalized sum of the Gaussian distribution of the prior information and a parameter θ defined in the HR frequency ranges of 0.7 Hz to 4 Hz; estimating the likelihood function for determining the current heart rate estimate, wherein the likelihood function is estimated by normalizing the spectrum of the modelled pulse signal corresponding to a current window; estimating the posterior probability of heart rate frequency by applying Bayes rule, wherein the posterior probability is estimated based on the prior information and the likelihood function; and estimating a current heart rate frequency, wherein the current heart rate frequency corresponds to the value at which posterior probability is maximum.

It is to be understood that both the foregoing general description and the following detailed description are exemplary and explanatory only and are not restrictive of the embodiments of the present disclosure, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 3A through FIG. 3E illustrate various stages in identifying a Region of Interest (ROI) from a frame, in accordance with an embodiment of the present disclosure.

FIG. 8A illustrates a Bland-Altman (BA) plot for a system known in the art disclosed by G. Balakrishnan et al. in a paper entitled "Detecting pulse from head motions in video".

FIG. 8B illustrates a Bland-Altman (BA) plot for a system known in the art disclosed by C. Huang et al. in a paper entitled "Accurate and efficient pulse measurement from facial videos on smartphones".

FIG. 8C through FIG. 8E illustrate Bland-Altman (BA) plots for modified versions System I, System II and System III respectively of the system of the present disclosure.

Figure 1:
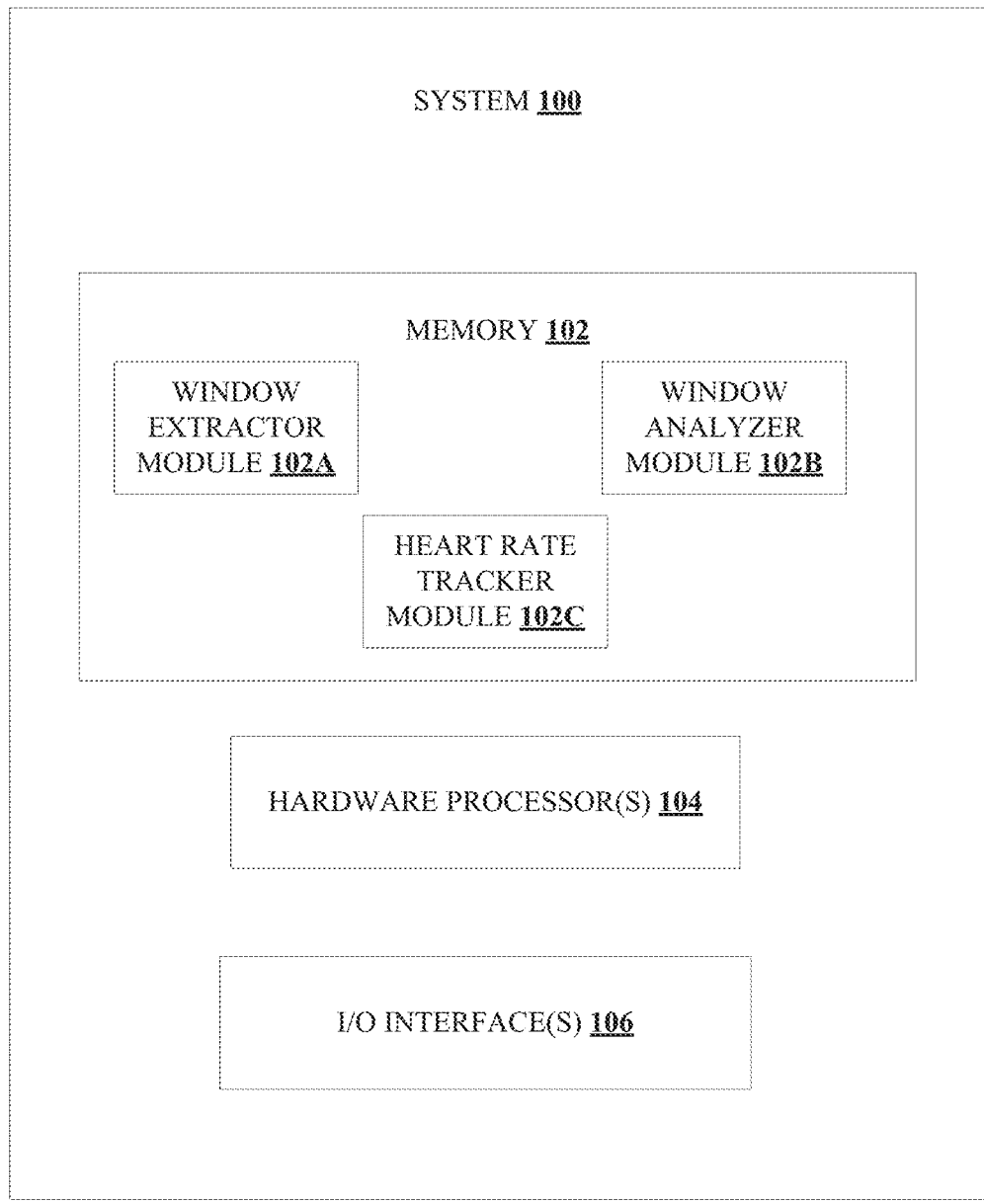
FIG. 1 is an exemplary block diagram of a system for face video based heart rate monitoring using pulse signal modelling and tracking, illustrating exemplary functional modules in accordance with an embodiment of the present disclosure.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Before setting forth the detailed explanation, it is noted that all of the discussion below, regardless of the particular implementation being described, is exemplary in nature, rather than limiting.

Traditional non-contact mechanisms require sophisticated, bulky, expensive and dedicated sensors like microwave doppler and laser for accurate heart rate (HR) monitoring. Modern non-contact mechanisms employ camera sensors for HR estimation. The camera sensors are not only portable and cheap but can also be used for other purposes. Face video based HR estimation is based on the fact that that heart beats generate cardiovascular pulse waves that propagate in the entire human body. It creates color variations in the reflected light which can be acquired from the camera. Moreover, micro-movements are produced in the vertical direction of the face due to the pressure exerted by the pulse when flowing from head to neck. These movements capturing the pulse information can be analyzed using the camera.

In the context of the present disclosure, the expression "face video" refers to a video wherein a face is detected in every frame. Any technique known in the art may be used to eliminate frames without a face, if any, and obtain an input video having the face in every frame.

Existing face based HR systems analyze the motion or color variations across time and refer them as temporal signals. The cardiovascular pulse is estimated from the temporal signals and eventually used for HR estimation. Along with the subtle pulse signal, the temporal signal constitutes prominent noise components originated due to: i) facial poses and expression variations; ii) unavoidable eye blinking; iii) face movements; iv) respiration; v) camera parameters (for example, change in focus); and vi) environmental factors (for example, illumination variations). These result in erroneous HR estimation. Moreover, most of the existing systems require huge time computation and hence these are not useful for real time applications. Systems and methods of the present disclosure alleviate these issues for improving HR monitoring.

Referring now to the drawings, and more particularly to FIGS. 1 through 10, where similar reference characters denote corresponding features consistently throughout the figures, there are shown preferred embodiments and these embodiments are described in the context of the following exemplary system and method.

FIG. 1 is an exemplary block diagram of a system 100 for face video based heart rate monitoring using pulse signal modelling and tracking, illustrating exemplary functional modules in accordance with an embodiment of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (102A through 102C) of the system 100 can be stored in the memory 102.

In an embodiment, the system 100 includes one or more data storage devices or memory 102 operatively coupled to the one or more processors 104 and is configured to store instructions configured for execution of steps of the method 200 by the one or more processors 104 via the exemplary one or more modules 102A through 102C.

Figure 2A:
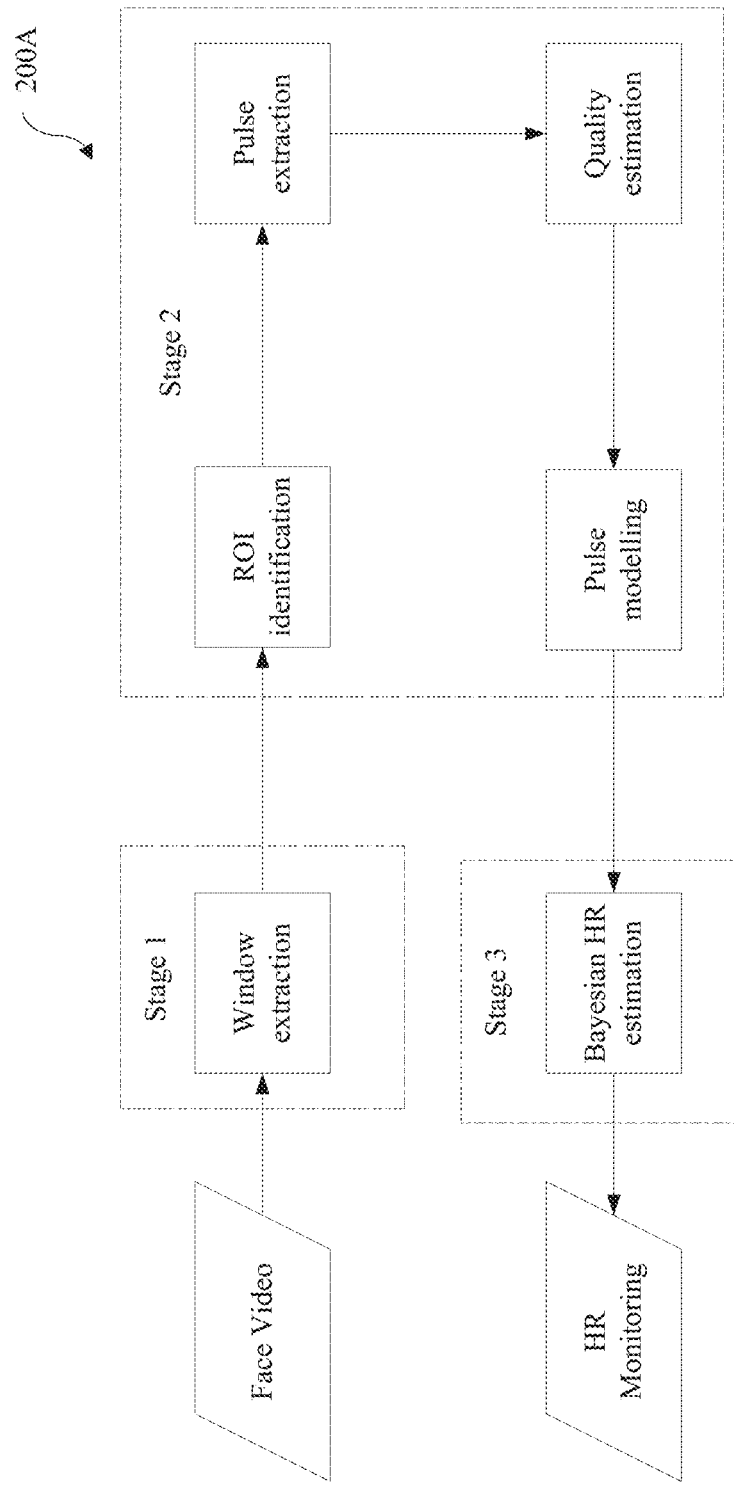
FIG. 2A is a high level flow chart illustrating key stages in a method for face video based heart rate monitoring using pulse signal modelling and tracking, in accordance with an embodiment of the present disclosure.
Figure 2B:
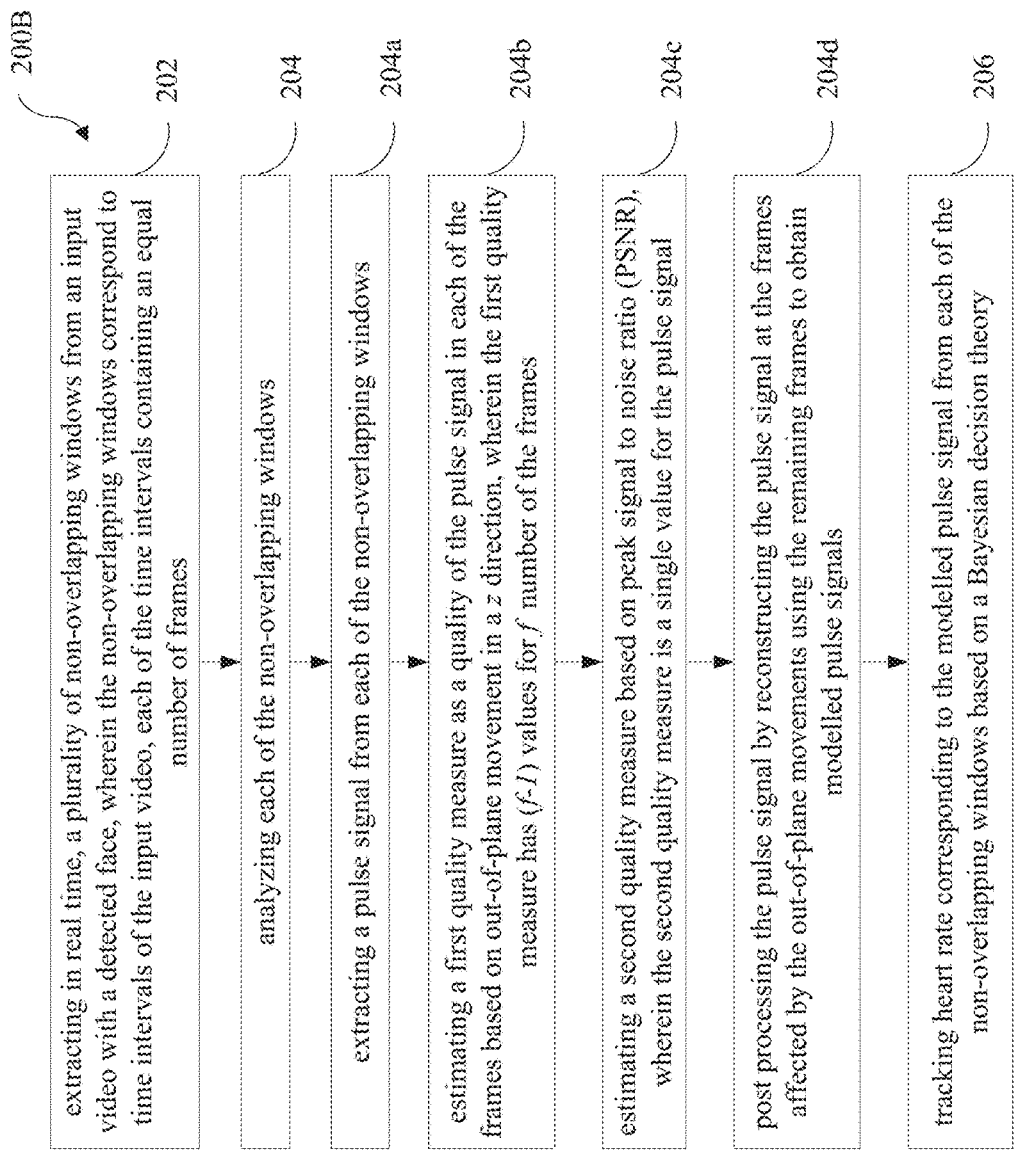
FIG. 2B is an exemplary flow diagram illustrating a computer implemented method for face video based heart rate monitoring using pulse signal modelling and tracking, in accordance with an embodiment of the present disclosure.

FIG. 2A is a high level flow chart 200A illustrating key stages in a method for face video based heart rate monitoring using pulse signal modelling and tracking and FIG. 2B is an exemplary flow diagram 200B illustrating a computer implemented method for the same, in accordance with an embodiment of the present disclosure. The steps of the method 200B will now be explained in detail with reference to the components of the system 100 of FIG. 1 and the key stages depicted in FIG. 200A. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

The face video based heart rate monitoring systems and methods of the present disclosure comprises three stages of operation as illustrated in FIG. 2A. On a high level, in Stage 1, the face video is divided into several non-overlapping windows. In Stage 2, a pulse signal is extracted after identifying a Region of Interest (ROI) and quality measures are estimated from each of the non-overlapping windows followed by pulse signal modelling. In Stage 3, Bayesian decision theory is used for HR estimation.

Accordingly, in an embodiment of the present disclosure, a window extractor module 102A is configured to extract in real time, at step 202, a plurality of non-overlapping windows from an input video with a detected face, wherein the non-overlapping windows correspond to time intervals of the input video, each of the time intervals containing an equal number of frames. The frames are eventually concatenated for HR monitoring.

In an embodiment of the present disclosure, a window analyzer module 102B is configured to analyze each of the non-overlapping windows, at step 204, wherein firstly a pulse signal is extracted from each of the non-overlapping windows at step 204a. Initially, ROIs are detected from the face video and problems due to in-plane face movements are minimized. Temporal signals are then extracted from the ROI. The temporal signals are used to estimate the spectrum associated with the pulse signal and quality of each of the non-overlapping windows. The pulse signal spectrum is further processed to minimize issues arising due to out-of-plane face movements.

FIG. 3A through FIG. 3E illustrate various stages in identifying the Region of Interest (ROI) from each frame, in accordance with an embodiment of the present disclosure. FIG. 3A illustrates an exemplary frame in an input video with a detected face. It contains non-face pixels which do not provide any HR related information; the non-face pixels are detected by applying skin detection and subsequently removed. FIG. 3B illustrates a skin mask from the exemplary frame of FIG. 3A. Unavoidable eye blinking can result in spurious HR estimation. Thus, the eye area needs to be detected from the face area in the detected face and subsequently removed. The facial landmarks are accurately estimated by applying Constrained Local Neural Fields (CLNF) and eye regions are obtained by finding the convex hull of facial landmarks corresponding to eyes and eyebrows. The resultant eye areas may be further dilated using morphological operations to compensate the error due to inaccurate facial landmark extraction. Subsequently, the dilated eye areas are removed. FIG. 3C illustrates facial landmarks on the detected face using CLNF and FIG. 3D illustrates removal of the eye area or region in the face area. FIG. 3E illustrates a resultant skin mask. It is observed that even subtle variations in face boundary pixels can significantly alter the temporal signals and thereby result in erroneous HR. Thus morphological erosion may be utilized to remove the face boundary pixels.

Uneven color variations and non-uniform impact of emotions on different face regions results in poor HR monitoring when full face is considered as one ROI. These issues are mitigated by methods of the present disclosure wherein after identifying the ROI corresponding to the detected face in each of the non-overlapping windows, the face area associated with the detected face is divided into non-overlapping square blocks. Face deformations are inevitable in the face video for various reasons such as face movements. The movements due to translation, rotation and scaling in any of the three directions (viz, in-plane x- and y-directions or out-of-plane z-direction), can shift the location of ROI and thus alter the temporal signals and eventually result in spurious HR estimation. Rectification of out-of-plane movements by stabilizing the ROI in the z-direction is error prone because it transforms the face in a different viewpoint that results in self-occlusion and partial face acquisition. In accordance with the present disclosure, in-plane transformations in the x and y directions are minimized to minimize ROI shifting by performing frame registration between a previous frame and a current frame within each of the non-overlapping windows based on a pre-defined subset of facial landmark points. In an embodiment, the pre-defined subset of facial landmark points may be facial landmark points belonging to the nose in the detected face since they are less affected by facial expressions as compared to remaining facial landmark points.

Figure 4A:
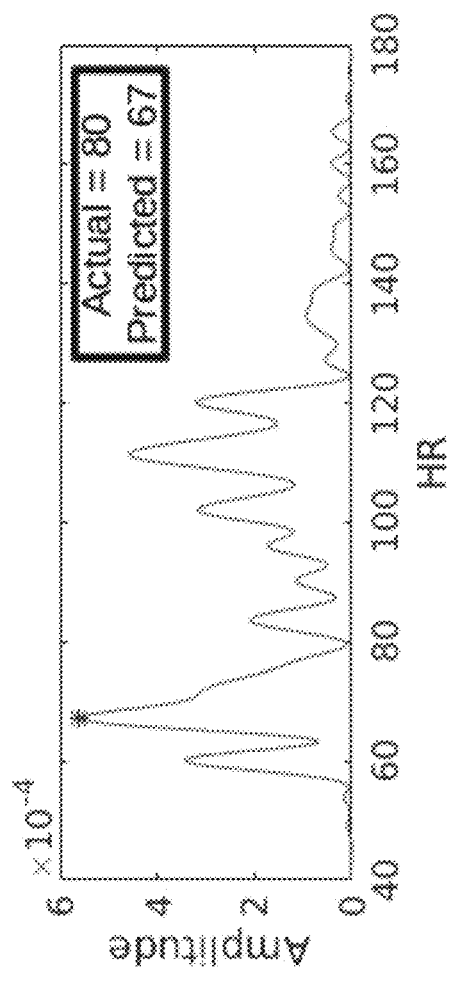
FIG. 4A and FIG. 4B illustrate spectrum of a pulse signal without frame registration and with frame registration in accordance with an embodiment of the present disclosure respectively.
Figure 4B:
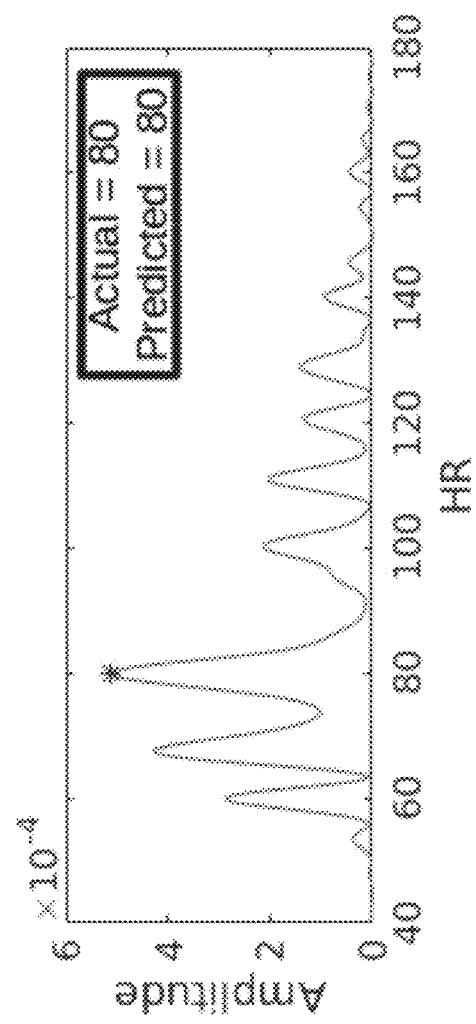

In accordance with the present disclosure, in-plane transformation in the x and y directions are obtained by minimizing the following constraint:

$$T^* = \arg\min_{T}\left[\sum_{i=1}^{q}\|F_i - T(M_i)\|_2\right] \rightarrow \quad (1)$$

where $M_i$ denotes the positions of $i^{th}$ nose landmark points in the current frame; $F_i$ denotes the position of $i^{th}$ nose landmark points in the previous frame; q is the number of nose landmark points; and T denotes the transformation matrix consisting of translations and rotation in 2-Dimension in the following manner:

$$\begin{bmatrix} \cos(\theta) & -\sin(\theta) & t_x \\ \sin(\theta) & \cos(\theta) & t_y \\ 0 & 0 & 1 \end{bmatrix} \rightarrow \quad (2)$$

where $\theta$ is the orientation while $t_x$ and $t_y$ are the translations in the x and y directions respectively. It may be noted that $M_i$ and $F_i$ denote positions of feature points in homogeneous coordinates, i.e. the feature at $[x,y]^T$ is represented by $[x,y,1]^T$. In an embodiment, gradient descent optimization method, as known in the art, may be utilized to solve equation (1). The face shifting in the x and y directions are minimized by registering the current frame using:

$$R = T(I_M) \quad (3)$$

where R is the registered image while $I_M$ is the current frame. FIG. 4A and FIG. 4B illustrate spectrum of a pulse signal without frame registration and with frame registration in accordance with an embodiment of the present disclosure respectively. It may be noted that HR is correctly estimated if frame registration is applied in accordance with the present disclosure as illustrated in FIG. 4B, else several spurious peaks result in erroneous HR as illustrated in FIG. 4A.

In accordance with the present disclosure, temporal signals are extracted from each of the non-overlapping square blocks of the ROI using Eulerian method, wherein the temporal signals correspond to motion or color variations in the detected face across time. It is known that out of RGB color channels, the strongest plethysmographic signal is present in the green channel. This may be leveraged by defining the temporal signal using the variations introduced in the average green channel intensities. Mathematically, the temporal signal $S^i$ corresponding to the $i^{th}$ ROI is given by:

$$S^i = [s_1^i, s_2^i, \ldots s_{(f-1)}^i] \quad (4)$$

where f denotes the total number of frames and $s_k^i$ represents variations in the average green channel intensities in $k^{th}$ frame for $i^{th}$ ROI, i.e., $$s_k^i = \sum_{(x,y) \in B^i} (F_{(k+1)}^g(x,y) - F_k^g(x,y)) \rightarrow \quad (5)$$

where $B^i$ represents the $i^{th}$ ROI; (x,y) denotes a pixel location; and $F_k^g$ stores the green channel intensities in $k^{th}$ frame.

In an embodiment, band-pass filter may be applied to remove noise in the extracted temporal signals. Since human heart beats within the range of 42 to 240 beat-per-minute (bpm), the frequency range of the filter may be set to 0.7 Hz to 4 Hz. Likewise, a de-trending filter, known in the art, may be subsequently applied to the filtered temporal signals for alleviating non-stationary trends. In accordance with the present disclosure, the pulse signal is then estimated from the temporal signals using a kurtosis based optimization method.

In accordance with the present disclosure, two different quality measures for pulse signal are estimated to improve the HR monitoring. In an embodiment, a first quality measure is estimated as a quality of the pulse signal in each of the frames based on out-of-plane movement in a z direction at step 204b. The first quality measure has (f–1) values for f number of the frames. A second quality measure is estimated based on peak signal to noise ratio (PSNR) at step 204c. The second quality measure is a single value for the pulse signal.

In accordance with the present disclosure, motion due to in-plane deformations has been managed by frame registration. But frames affected by out-of-plane motions can result in self-occlusion and thereby erroneous temporal signal and pulse signal. Thus, the quality of pulse signal which indicates the confidence in correct estimation, is defined by the out-of-plane movements, i.e., changes of facial landmark locations in z-direction. The facial landmark points that are highly affected by the motion in z-direction are chosen to evaluate the variations. In accordance with the present disclosure, for estimating a first quality measure firstly a deviation introduced by a change of location of pre-defined facial landmark points in the z direction is calculated, wherein the deviation is calculated between each pair of consecutive frames in each of the non-overlapping windows. In an embodiment, the pre-defined facial landmark points are the points lying on the face boundaries as illustrated in FIG. 3C. Consider that $k^{th}$ and $(k-1)^{th}$ denote the current and previous frame respectively; $l_k^j$ denote the z-coordinate of $j^{th}$ chosen landmark on $k^{th}$ frame; and $l_{k-1}^j$ denote the z-coordinate of $j^{th}$ chosen landmark on $(k-1)^{th}$ frame. It may be observed that deviations in both positive and negative directions are introduced during head motion in the z-direction, thus maximum absolute change in the z-direction provides the deviation using $$d_{(k-1)} = \max(|l_k^j - l_{k-1}^j|) \quad (6)$$

where $d_{(k-1)}$ denote the deviation introduced in the $k^{th}$ frame; |●| is the absolute operator; and max provides the maximum value. After evaluating the deviations for all possible frames, the first quality measure at $(k-1)^{th}$ frame, $\hat{q}_{(k-1)}$ is evaluated using:

$$\hat{q}_{(k-1)} = 1 - \left(\frac{d_{(k-1)} - \min(d)}{\max(d) - \min(d)}\right) \rightarrow \quad (7)$$

where d represents deviations in all the frames and is given by $$d = [d_1, d_2, \ldots d_{f-1}] \quad (8)$$

where f is the number of frames. In essence, $d_{(k-1)}$ in equation (7) is first normalized to [0,1] and then modified to define quality such that low and high deviations results in high and low quality values respectively. Thus the quality due to out-of-plane movements, $\hat{Q}$ is given by:

$$\hat{Q} = [\hat{q}_1, \hat{q}_2, \ldots \hat{q}_{(f-1)}] \quad (9)$$

Figure 5A:
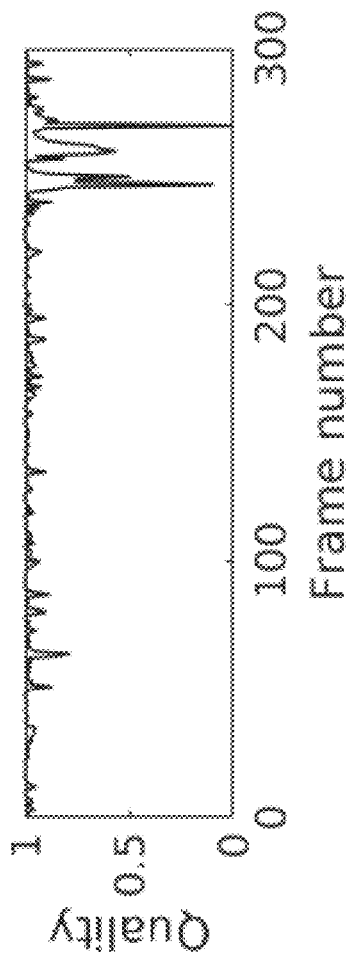
FIG. 5A illustrates an exemplary quality estimation using out-of-plane movements in accordance with an embodiment of the present disclosure.

FIG. 5A illustrates an exemplary quality $\hat{Q}$ estimation using out-of-plane movements in accordance with an embodiment of the present disclosure.

The second quality measure is estimated based on peak signal to noise ratio (PSNR) as known in the art. Typically, the amplitude of a pulse spectrum contains a peak at the HR frequency and negligible values at other frequencies. Unfortunately, in the pulse spectrum, the noise increases the amplitude at other frequencies. Thus, PSNR can be defined such that the signal can be interpreted as the amplitudes corresponding to HR frequency while noise can be thought of the amplitudes at the remaining frequencies. Mathematically, the second quality measure given by PSNR, q is given by:

$$q = \frac{\sum_{i=maxLoc(S_p)-n_p}^{maxLoc(S_p)+n_p} S_p(i)}{\overline{sum}(S_p) - \sum_{i=maxLoc(S_p)-n_p}^{maxLoc(S_p)+n_p} S_p(i)} \rightarrow \quad (10)$$

where $S_p$ denotes the spectrum of the estimated pulse signal; $\overline{sum}$ performs the sum over all the frequencies; $n_p$ represent the neighborhood size; and maxLoc returns the position containing the maximum value, thus the location of HR frequency is given by $maxLoc(S_p)$. The signal (numerator) in equation (10) is obtained by adding the amplitude of HR frequency and its few neighborhoods while noise (denominator) is obtained by adding the amplitude of the remaining frequencies.

Figure 5B:
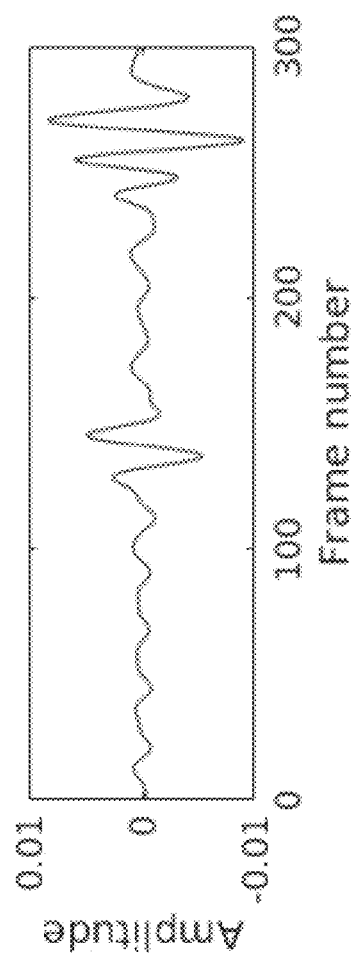
FIG. 5B and FIG. 5C illustrate a pulse signal and corresponding spectrum respectively, wherein the pulse signal is contaminated by out-of-plane movements.
Figure 5C:
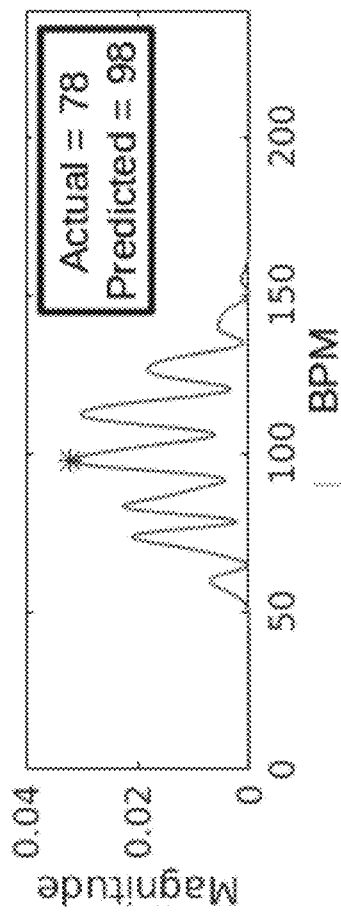

The frames affected by out-of-plane movements may result in spurious temporal signal estimation and thereby deteriorate pulse signal estimation, $\overline{X}_e$. FIG. 5B and FIG. 5C illustrate a pulse signal and its corresponding spectrum respectively, wherein the pulse signal is contaminated by out-of-plane movements. It may be noted from FIG. 5C that the predicted HR is deviated significantly from the actual HR. To improve the efficacy of the pulse signal, in accordance with an embodiment of the present disclosure, at step 204d, Fourier basis function based modelling of pulse signal is performed to reconstruct the pulse signal at those frames that are affected by out-of-plane movements using the other frames to obtain modelled pulse signals. The problem of noise reduction is formulated as a data fitting problem which consists of: i) pulse signal approximation using appropriate basis function; ii) fitting parameters evaluation; and iii) pulse signal reconstruction using the Fourier basis function and model (or fitting) parameters.

Mathematically, $\overline{X}_e$ can be decomposed as:

$$\overline{X}_e(x) \approx \sum_{i=1}^{\infty} a_i \phi_i(x) \rightarrow \quad (11)$$

wherein $\propto$ is the number of Fourier basis function; $a_i$ denotes the model parameter for $i^{th}$ parameter; x denotes the frame number; and $\varnothing_i(x)$ is the $i^{th}$ basis function. For simplicity, the equation (11) may be written in a matrix form using:

$$\overline{X}_e \approx A\phi \rightarrow \quad (12)$$

$$\text{where } \phi = \begin{bmatrix} \phi_1(1) & \phi_2(2) & \dots & \phi_1(f-1) \\ \phi_2(1) & \phi_2(2) & \dots & \phi_2(f-1) \\ \vdots & \vdots & & \vdots \\ \phi_\infty(1) & \phi_\infty(2) & & \phi_\infty(f-1) \end{bmatrix} \quad (13)$$

and $$A = [a_1, a_2, \dots . a_\infty] \quad (14)$$

Basis function stored in $\phi$ are defined using the Fourier basis function because (i) these basis are orthogonal which provides stability in the optimization by assuring low residual error; and (ii) their amplitude lies in the range [−1,1] which helps in avoiding the problem of overflowing integer as with polynomial basis. The Fourier basis function for the order n are given by:

$$\phi_n(x) = \begin{cases} \sin\left(\frac{(n+1)}{2} \times x\right) & \text{if } n \text{ is odd} \\ \cos\left(\frac{n}{2} \times x\right) & \text{if } n \text{ is even} \end{cases} \rightarrow \quad (15)$$

There are $\propto$ unknown parameters and (f−1) observations (or number of frames). The overdetermined system of linear equation shown in equation (12) can be solved by the least square method. To avoid the influence of out-of-plane movements during modelling, weighted least square equation is utilized where weights are given by the quality due to out-of-plane movements, $\hat{Q}$. That is, $$\hat{A} = \arg\min_A \left\| \hat{Q}(\overline{X}_e - A\phi) \right\|_2 \rightarrow \quad (16)$$

where $\hat{A}$ contains the estimated modelling parameters; $\|\bullet\|$ contains the norm; $(\overline{X}_e - A\phi)$ denotes an associated reconstruction error and $\hat{Q}$ (solved in equation (9) is the quality due to out-of-plane movements based on first quality measure. The solution of equation (16) is given by:

$$\hat{A} = (\phi^T \overline{Q} \phi)^{-1} \phi^T \overline{Q} \overline{X}_e \quad (17)$$

where $\overline{Q}$ is a diagonal matrix formed from $\hat{Q}$ in the following manner:

$$\overline{Q} = \text{diag}(\hat{q}_1, \hat{q}_2, \dots \hat{q}_{(f-1)}) \quad (18)$$

The modelled pulse signal, $\hat{X}_e$ is obtained based on the estimated modelling parameters and the Fourier basis function and represented in an embodiment as a product as shown below:

$$\hat{X}_e = \hat{A}\phi \quad (19)$$

Figure 5D:
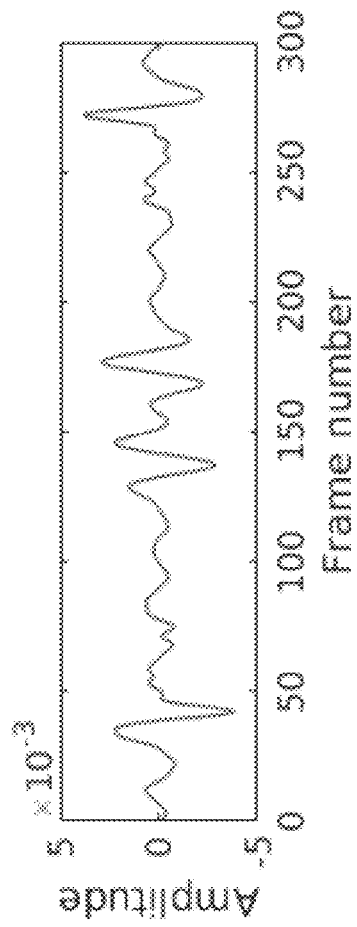
FIG. 5D illustrates a modelled pulse signal based on Fourier basis function based modelling of the pulse signal in accordance with an embodiment of the present disclosure.
Figure 5E:
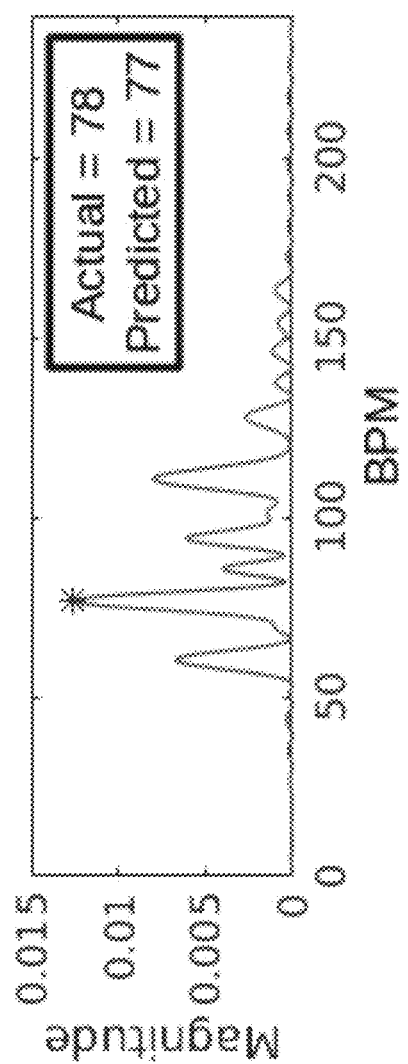
FIG. 5E illustrates a spectrum of the modelled pulse signal of FIG. 5D.

FIG. 5D illustrates a modelled pulse signal based on Fourier basis function based modelling of the pulse signal in accordance with an embodiment of the present disclosure and FIG. 5E illustrates an associated spectrum of the modelled pulse signal.

It may be observed from FIG. 5C and FIG. 5E that the HR estimation improves significantly after incorporating the Fourier based modelling in accordance with the present disclosure. The spectrum of noise-free pulse signal should contain maximum amplitude at the frequency corresponding to the HR but the phenomenon is often violated when noise is present in the pulse signal. Filtering and modelling techniques do not remove noise completely from the pulse signal due to which the estimated pulse signal contains several spurious peaks. In an embodiment of the present disclosure, a heart rate (HR) tracker module 102C is configured to track heart rate corresponding to the modelled pulse signal, at step 206, from each of the non-overlapping windows based on a Bayesian decision theory, wherein the modelled pulse signal may be corrupted by noise. In accordance with the present disclosure, the step of tracking HR comprises estimating the heart rate using the Bayesian decision theory by estimating a current heart rate corresponding to a current modelled pulse signal using previous heart rate of a preceding modelled pulse signal and the second quality measure associated with the current and the preceding modelled pulse signals; and analyzing a spectrum associated with the modelled pulse signal from each of the non-overlapping windows to identify frequency of a maximum amplitude corresponding to the heart rate thereof as an HR frequency.

Usually, a small HR change is observed between the HRs belonging to the consecutive windows. In accordance with the present disclosure, the previous HR is thus utilized in defining prior knowledge. The prior knowledge is defined such that a large value is provided when the deviation between the current HR and previous HR estimates is small while a small value is provided when the deviation is large. Moreover, it is intuitive that if the previous HR estimate is spurious, the error can be propagated in the subsequent HR. Hence in such cases, it is better to utilize low prior information about the previous HR for the current HR estimation. Accordingly, the measure of confidence in the previous HR estimate is defined based on the quality of the previous HR estimate utilizing the second quality measure. Thus prior information required for $(i+1)^{th}$ window is given by:

$$P_g(\theta) = \frac{q_i}{\sqrt[c]{2\pi}} \exp\left[\left(\frac{q_i}{c}(\theta - h_i)\right)^2\right] \sim \mathcal{N}\left(h_i, \frac{c}{q_i}\right) \rightarrow \quad (20)$$

where $h_i$ and $q_i$ denote the heart rate frequency and the second quality measure estimated in the previous window (i.e. $i^{th}$ window); c is a pre-defined constant; and $\theta$ stores the probable HR frequencies ranging from 0.7 Hz to 4 Hz for the current $(i+1)^{th}$ window. In case the first window is analyzed (i.e., i=0), the $q_i$ is set to zero, so that all the values are equally likely and hence no useful prior information is provided. It may be observed that Gaussian distribution $\mathcal{N}$ is used in equation (20) such that mean and variance are given by $h_i$ and $$\frac{c}{q_i}$$

respectively. Thus, small quality results in high variance which in turn results in low prior knowledge.

The problem in defining the prior information using equation (20) is that it strictly restricts the large deviation from the previous HR. To handle the issue, significant values are added in the plausible HR frequencies in the present disclosure. That is, prior information is modified using:

$$P_e(\theta) = \begin{cases} \dfrac{P_u(\theta) + P_g(\theta)}{Z_1}, & \text{if } 0.7 < \theta < 4 \text{ Hz} \\ 0, & \text{otherwise} \end{cases} \rightarrow \quad (21)$$

where $P_e$ denotes the modified prior information and $P_g$ is the distribution described in equation (20). Remaining parameters $Z_1$ and $P_u$ are introduced to normalize $P_e$ and reducing the frequency differences respectively. These are given by:

$$Z_1 = \sum_{\theta=0.7}^{4} (P_u(\theta) + P_g(\theta)) \rightarrow \quad (22)$$

and $$P_u(\theta) = \begin{cases} 0.5, & \text{if } 0.7 < \theta < 4 \text{ Hz} \\ 0, & \text{otherwise} \end{cases} \quad (23)$$

In essence, $P_u$ is defined in the HR frequency ranges of 0.7 Hz to 4 Hz such that any value is equally probable.

The likelihood function is denoted by $P_l(S_{i+1}|\theta$ where $S_{i+1}$ denote the spectrum of the reconstructed pulse signal $\hat{X}_e$ corresponding to the $(i+1)^{th}$ window. It is estimated by normalizing the spectrum, $S_{i+1}$, i.e.

$$P_l(S_{i+1}|\theta = \dfrac{S_{i+1}(\theta)}{\sum_{\theta=0.7}^{4Hz} S_{i+1}(\theta)} \rightarrow \quad (24)$$

The posterior probability, $P_p(\theta|S_{i+1})$ is evaluated using the likelihood function by applying the Bayes rule, i.e.

$$P_p(\theta|S_{i+1}) = \dfrac{P_l(S_{i+1}|\theta)P_e(\theta)}{P(S_{i+1})} \rightarrow \quad (25)$$

where $P(S_{i+1})$ is the evidence factor. Equations (21), (24) and (25) can be combined in the following manner:

$$P_p(\theta|S_{i+1}) = \dfrac{S_{i+1}(\theta)(P_u(\theta) + P_g(\theta))}{Z_2} \rightarrow \quad (26)$$

where $Z_2$ is a normalization coefficient given by:

$$Z_2 = Z_1 . P(S_{i+1}) . \left( \sum_{\theta=0.7}^{4Hz} S_{i+1}(\theta) \right) \rightarrow \quad (27)$$

Figure 6A:
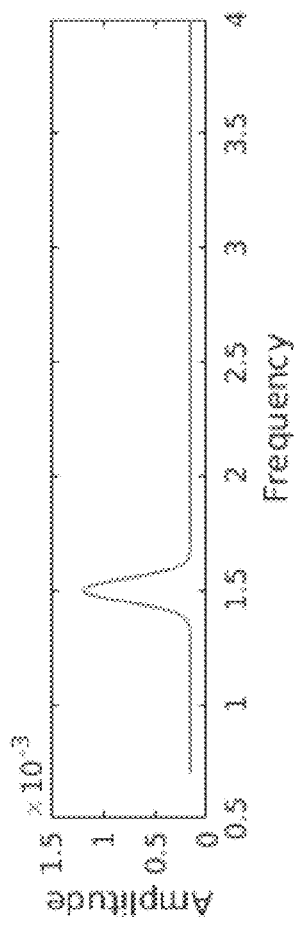
FIG. 6A through FIG. 6C illustrate estimated prior information, likelihood function and corresponding posterior probability for HR tracking respectively in accordance with an embodiment of the present disclosure.
Figure 6B:
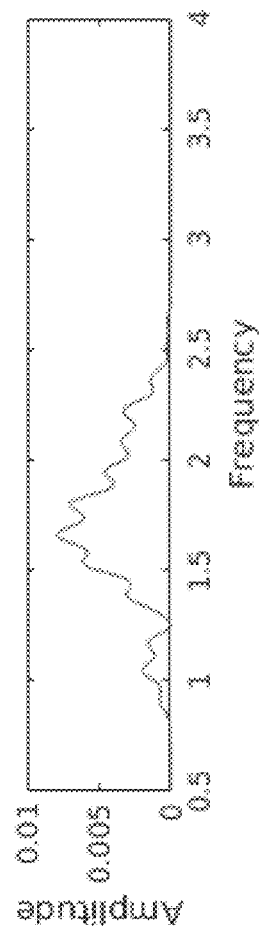
Figure 6C:
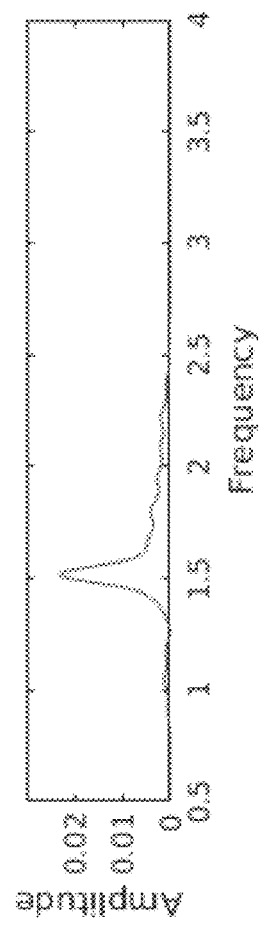

FIG. 6A through FIG. 6C illustrate estimated prior information, likelihood function and corresponding posterior probability for HR tracking respectively in accordance with an embodiment of the present disclosure. A maximum a posteriori estimation is utilized to estimate the HR frequency. It provides the minimum-error-rate classifier based on zero-one loss function. For brevity, the expected loss incurred on selecting a particular frequency, d is given by:

$$R(\theta = d|S_{i+1}) = \sum_{K=0.7}^{4} L(d, \theta) P_p(\theta = K|S_{i+1}) \rightarrow \quad (28)$$

where R is the incurred loss and L represents the loss function given by:

$$L(d, \theta) = \begin{cases} 0, & \text{if } \theta = d \\ 1, & \text{otherwise} \end{cases} \rightarrow \quad (29)$$

Further, it is obvious that the sum of likelihood function at all the possible values (which lies between 0.7 Hz to 4 Hz) will be equal to one, i.e., $$\sum_{K=0.7}^{4} P_p(\theta = K|S_{i+1}) = 1 \rightarrow \quad (30)$$

It may be seen by combining equations (28), (29) and (30) that:

$$R(\theta = d|S_{i+1}) = 1 - P_p(\theta = d|S_{i+1}) \quad (31)$$

It points out that for minimum expected loss, R, value of $\theta$ may be chosen such that the posterior probability $P_p$ is maximized. Hence, the frequency corresponding to HR in $(i+1)$th window, $h_{i+1}$ is given by:

$$h_{i+1}(x) = \underset{\theta}{\arg\max} \, P_p(\theta|S_{i+1}) \rightarrow \quad (32)$$

Figure 7:
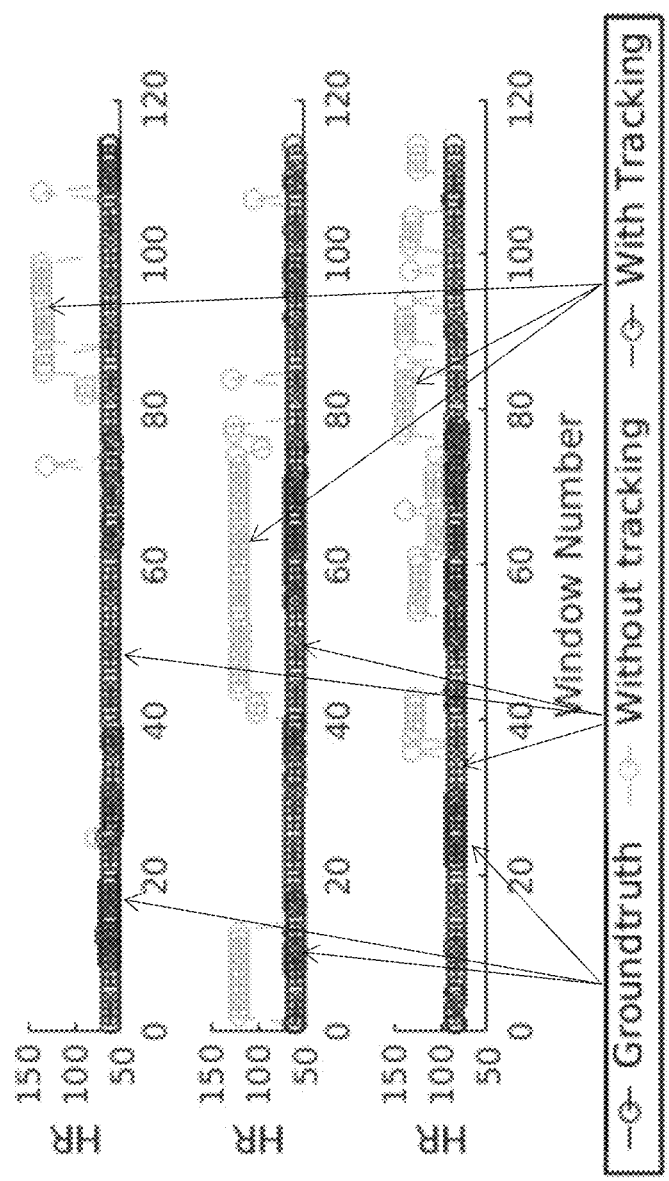
FIG. 7 illustrates HR monitoring without tracking and with tracking in accordance with an embodiment of the present disclosure.

Subsequently, the HR is given by:

$$\hat{H}(i+1) = \text{round}(h_{i+1} \times 60) \quad (33)$$

where round operator rounds off the value to the nearest integer. FIG. 7 illustrates HR monitoring without tracking and with tracking in accordance with an embodiment of the present disclosure. The actual HR monitoring along with the predicted HR monitoring when tracking is avoided and applied respectively may be seen from FIG. 7. It demonstrates that the HR monitoring is improved significantly when HR tracking is used.

Experimental Results

Data Recording: The performance of the system of the present disclosure was evaluated on Intel™ i5-2400 CPU 3.10 GHz. A total of 50 face videos were collected from 50 different subjects. The videos were acquired from Logitech webcam C270 camera which was mounted on a laptop and the subjects were free to perform natural facial movements, for example eye blinking, smiling and slight head pose variations. These were acquired under natural illumination at 28 frames per second and their total duration is 54 second. The ground truth was obtained by simultaneously acquiring the actual pulse from the right index fingertip using CMS 50D+ pulse oximeter.

Performance Measurement: Several metrics are used for the performance evaluation. Consider $\overline{P}(i,j)$ and $\overline{A}(i,j)$ denote the predicted and actual HR estimates respectively for $i^{th}$ subject in $j^{th}$ window. The descriptions of the performance metrics are as follows:

1) Bland-Altman (BA) plot is used to depict the agreement between actual and predicted measurements. That is, the abscissas and ordinate of the BA plot is given by average HR (viz., $$\frac{\overline{P}(i,j)+\overline{A}(i,j)}{2}$$

and prediction error (viz., $\overline{P}(i,j)-\overline{A}(i,j)$ respectively. An HR monitoring system can be considered accurate when the predicted HR estimates are closer to actual HR estimates, i.e., the prediction error shown as the ordinate of BA plot is closer to zero. In essence, the mean and variance of the prediction error are close to zero. Thus, the following five measures are analyzed for the evaluation: i) mean μ of HR error; ii) standard deviation σ of HR error; iii) percentage of samples with absolute error less than 5 bpm, $err_5$; iv) percentage of samples with absolute error less than 10 bpm, $err_{10}$; and v) percentage of samples with absolute error less than 15 bpm, $err_{15}$.

2) The mean average error, MAE of all the subjects which is given by:

$$MAE = \frac{\sum_{i=1}^{z}\sum_{j=1}^{n_i}|\overline{P}(i,j)-\overline{A}(i,j)|}{\sum_{i=1}^{z}n_i} \rightarrow \quad (34)$$

where |●| is the absolute operator; $n_i$ represent the number of windows for $i^{th}$ subject; and z is the total number of subjects. Lower value of MAE indicates that the predicted and estimated HR estimates are close to each other.

3) The Pearson correlation coefficient ρ evaluates similarity between two variables in terms of linear relationship and it lies between −1 to 1. It is given by:

$$\rho = \frac{cov(\overline{P},\overline{A})}{\sigma_{\overline{P}}\sigma_{\overline{A}}} \rightarrow \quad (35)$$

where cov and σ are the covariance and standard deviation operator respectively. Better HR estimation requires high similarity between the predicted and actual HR, i.e. high ρ.

4) Other metrics used are mean and standard deviation of average absolute error and average absolute error percentage. The average absolute error, $err_1(i)$ for $i^{th}$ subject is given by:

$$err_1(i) = \frac{1}{n_i}\sum_{j=1}^{n_i}|\overline{P}(i,j)-\overline{A}(i,j)| \rightarrow \quad (36)$$

The mean and standard deviation of $err_1$ for all the subjects are denoted by $err_1^m$ and $err_1^s$ respectively.

Similarly, average absolute error percentage, $err_2(i)$ for $i^{th}$ subject is given by:

$$err_2(i) = \frac{1}{n_i}\sum_{j=1}^{n_i}\frac{|\overline{P}(i,j)-\overline{A}(i,j)|}{\overline{A}(i,j)} \rightarrow \quad (37)$$

The mean and standard deviation of $err_2$ for all the subjects are denoted by $err_2^m$ and $err_2^s$ respectively. Units of $err_1^m$ and $err_1^s$ are in bpm. Good HR monitoring requires lower values of $err_1^m$, $err_1^s$, $err_2^m$ and $err_2^s$.

5) Apart from the accuracy, time required is another crucial parameter to understand the efficacy. Thus, computational time, $t_s$ is used as a performance metrics which is the time required for HR monitoring in seconds Implementation details: The time window was chosen such that each window contains 240 number of frames and the overlap between subsequent windows is about 230 frames. The order n required during modelling was set to be 50. It is important to note that the basis required for the computation are precomputed and stored rather than computing during the experimentation so as to save the computational time.

Figure 8E:
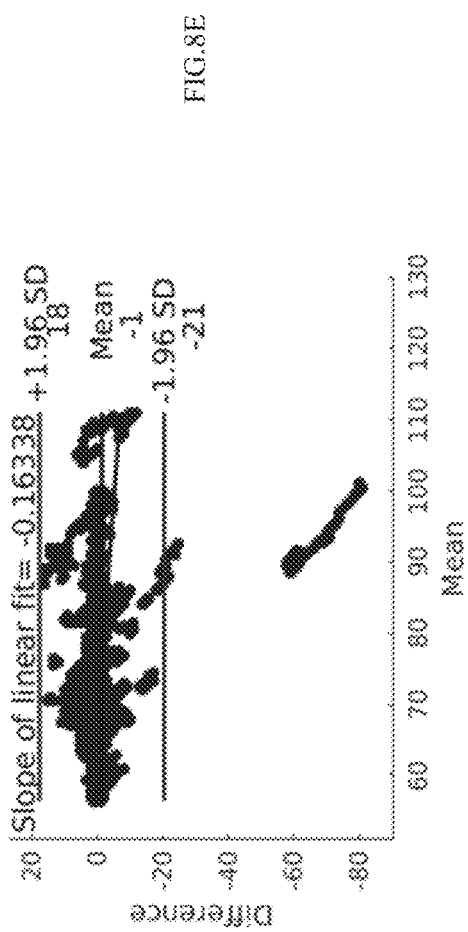
Figure 8F:
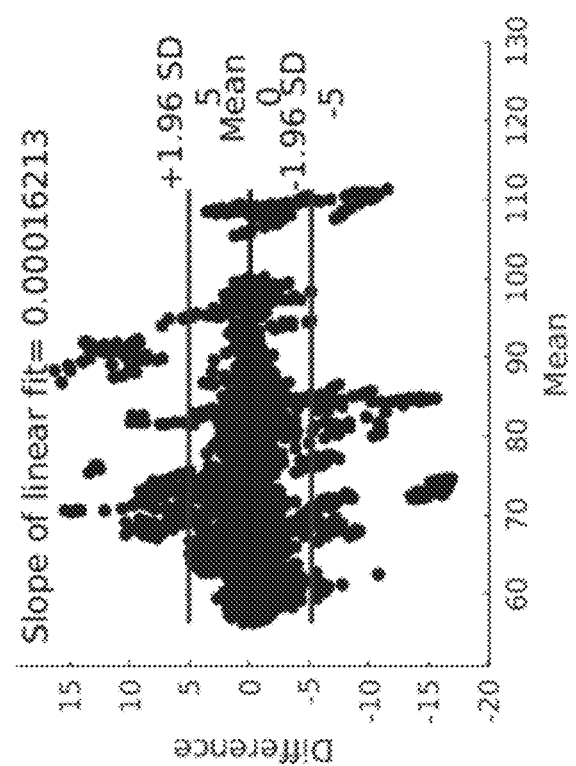
FIG. 8F illustrates a Bland-Altman (BA) plot for the system of the present disclosure.

Performance Evaluation: For better understanding of the effectiveness of pulse modelling and HR tracking in the system of the present disclosure, the following three systems are considered to evaluate the performance, viz., a) System I which is obtained by avoiding pulse modelling and HR tracking in the system of the present disclosure; b) System II which is obtained by considering pulse modelling but avoiding HR tracking in the system of the present disclosure; and c) System III which is the resultant when pulse modelling is avoided, but HR tracking is considered in the system of the present disclosure. Well known systems known in the art are also used for the evaluation. A system disclosed in a paper entitled "Detecting pulse from head motions in video" by G. Balakrishnan et al. based on Lagrangian temporal signals, i.e., discriminating facial features are explicitly tracked over time has been used; pulse signal is extracted from the temporal signals using Principal Component Analysis. Another system disclosed in a paper entitled "Accurate and efficient pulse measurement from facial videos on smartphones" by C. Huang et al. registers the face, followed by the evaluation of Eulerian temporal signals. It averages all the temporal signals for pulse extraction and thus, avoids the time-consuming blind source separating techniques. It may be noted that the systems disclosed by G. Balakrishnan et al. and C. Huang et al. that have been used for the evaluation are designed to provide one HR value instead of providing HR in multiple windows. To conform these systems with the system of the present disclosure, the pulse signal is first estimated and then analyzed in windows for monitoring. The performance metrics for the systems are presented in Table IA, Table IB and the corresponding BA-plots are depicted in FIG. 8A through FIG. 8E wherein particularly, FIG. 8A illustrates a Bland-Altman (BA) plot for the system disclosed by G. Balakrishnan et al.; FIG. 8B illustrates a Bland-Altman (BA) plot for the system disclosed by C. Huang et al.; FIG. 8C through FIG. 8E illustrate Bland-Altman (BA) plots for modified versions System I, System II and System III respectively of the system of the present disclosure; and FIG. 8F illustrates a Bland-Altman (BA) plot for the system of the present disclosure.

TABLE IA

Comparative results of HR monitoring

| System | μ | σ | $err_5$ | $err_{10}$ | $err_{15}$ | MAE |
|---|---|---|---|---|---|---|
| G. Balakrishnan et al. | −18.4092 | 27.6186 | 36 | 47 | 55 | 22.5960 |
| C. Huang et al. | −9.0733 | 20.2522 | 76 | 79 | 81 | 10.0305 |

TABLE IA-continued

Comparative results of HR monitoring

| System | μ | σ | $err_5$ | $err_{10}$ | $err_{15}$ | MAE |
|---|---|---|---|---|---|---|
| I | −6.4388 | 17.4399 | 82 | 85 | 86 | 7.3826 |
| II | −6.1794 | 17.1003 | 82 | 85 | 86 | 7.1857 |
| III | −1.4869 | 9.7057 | 92 | 96 | 97 | 2.7165 |
| Present disclosure | −0.1044 | 2.6177 | 93 | 98 | 100 | 1.3299 |

TABLE IB

Comparative results of HR monitoring (contd.)

| System | ρ | $err_1^m$ | $err_1^s$ | $err_2^m$ | $err_2^s$ | $t_s$ |
|---|---|---|---|---|---|---|
| G. Balakrishnan et al. | −0.0797 | 22.5960 | 16.6229 | 32.7984 | 25.9938 | 25.72 |
| C. Huang et al. | 0.3526 | 10.0305 | 10.7058 | 14.4150 | 16.3654 | 30.37 |
| I | 0.4493 | 7.3826 | 8.8127 | 10.5811 | 13.4582 | 6.84 |
| II | 0.4613 | 7.0299 | 8.6626 | 10.0478 | 13.2352 | 9.63 |
| III | 0.7132 | 2.6724 | 9.0489 | 3.9766 | 15.1524 | 7.06 |
| Present disclosure | 0.9751 | 1.3291 | 1.0830 | 1.7648 | 1.3889 | 9.78 |

It can be inferred from the Table IA, IB and FIGS. 8A through 8F that:

1) The system by G. Balakrishnan et al. exhibits the lowest performance in terms of both monitoring and time computations. Reason behind such behavior is the computationally expensive and erroneous feature tracking. It considers only the forehead, nose and mouth areas out of which forehead areas do not consider much discriminating features and mouth features are easily affected by facial expressions like smiling. Such factors results in error-prone tracking. It is observed that few features are available that are tracked in all the frames and even they are error-prone. Typically, these numbers of features lie between 5 and 18 and most of them belong to the forehead and nose areas.

2) The system by C. Huang et al. demonstrates lower performance than the other systems except the system by G. Balakrishnan et al. It averages all the temporal signals for pulse extraction which is error prone because the amplitude of pulse signal and noise in temporal signal of the different face regions depend on the facial structure and facial expressions. This is the major reason for the erroneous HR. It is obvious that system by C. Huang et al. saves large time computations by avoiding the blind source separation yet it is highly time consuming because of the face tracking for face registration. Out of the total 30.37 seconds, the average time required for the tracking is 25.87 seconds.

3) System I performs better than the systems by G. Balakrishnan et al. and C. Huang et al. by selecting appropriate tracking, blind source separation and Eulerian temporal signals. It requires average time of 6.84 second for the computations out of which blind source separation is the most time consuming, requiring 5.13 seconds. It is important to remember that the quality due to out-of-plane movements is not required in the System I and hence, avoided.

4) System II provides better HR monitoring than System I because it mitigates the problems due to out-of-plane movements by modelling the pulse signal. As compared to System I, the modelling and quality estimation due to out-of-plane movements in System II incurred an additional average time of 2.79 sec, out of which the quality estimation requires average time of 2.48 sec.

5) System III performs significantly better HR monitoring than System I because it considers the prior knowledge of the HR estimates to improve the current HR estimates in case of pulse signal is affected by noise. Moreover, it can be seen that it requires PSNR based quality estimation which requires low time computations as opposed to the quality estimation in System II. Hence, System III incurs an additional average time of 0.22 sec when compared with System I.

6) The system of the present disclosure which incorporates both the pulse modelling and tracking in the System I provides best HR monitoring amongst all the systems. It incurs an additional average time of 2.94 sec when compared with System I due to modelling and tracking. Majority of the additional time is taken by the quality estimation due to out-of-plane movements. In order to achieve the significantly better HR monitoring, the small time difference can be neglected for the face videos of 54 sec.

There exist some wrist contact systems in the art which incorporate previous HR for better HR monitoring. The system of the present disclosure differs from these systems in the sense that it is applicable for face videos based HR monitoring and it also incorporates quality of the HR along with the previous HR estimates. Face based and wrist contact based HR monitoring systems rely on different methodologies thus, wrist contact systems cannot be directly applied for face based HR monitoring. The noise sources and noise attributes in wrist contact and face based HR monitoring are different. Unlike face videos based monitoring, hand motion generates the noise in wrist contact based monitoring which can be estimated using accelerometer and removed for better HR monitoring. Moreover, slight motion in wrist contact based HR remains unaffected because the contact between skin and sensor remains intact. However, it can significantly deteriorate the face based HR monitoring. Pulse signal cannot be recorded when motion causes a gap between the human skin and the sensors. It results in non-existence of HR. Such problems usually do not arise in face based HR monitoring. The amplitudes of the spectral peaks corresponding to HR also remain nearly same in wrist contact based HR when the contact is maintained. However, they are highly fluctuating for face based HR because of the facial pose and expression variations.

Figure 9:
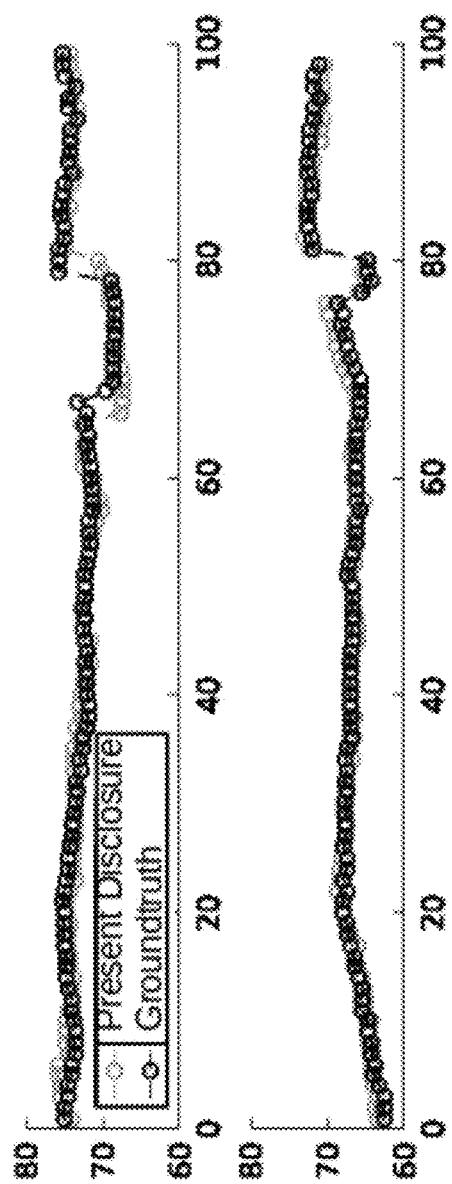
FIG. 9 illustrates HR monitoring by an embodiment of the system of the present disclosure under large HR deviations.
Figure 10:
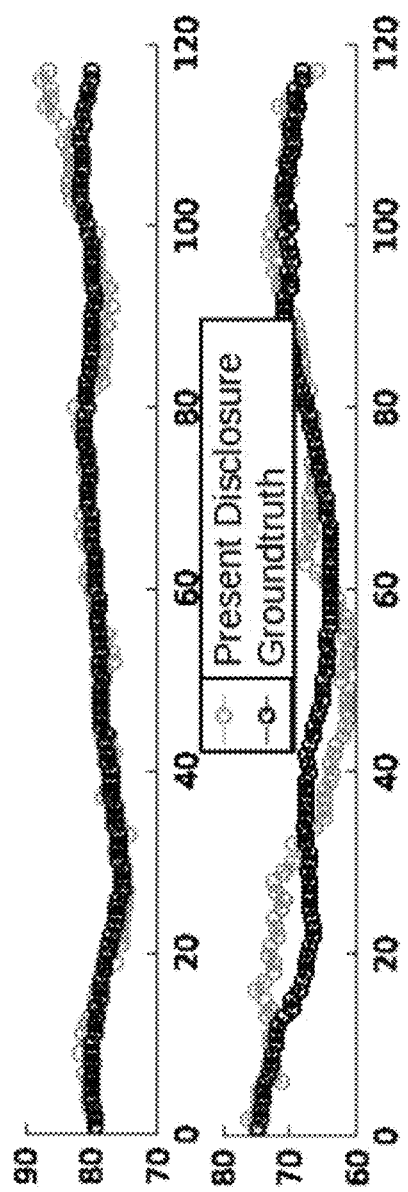
FIG. 10 illustrates erroneous HR monitoring by an embodiment of the system of the present disclosure.

The system of the present disclosure incorporates HR tracking which aims to correctly estimate the current HR by utilizing the previous HR and quality estimates. It is based on the assumption that the deviation between the current HR and previous HR should not be large. The system of the present disclosure can withstand the large deviation provided the pulse signal does not possess poor quality. FIG. 9 illustrates HR monitoring by an embodiment of the system of the present disclosure where the problem of large HR deviations has been alleviated. However, like other systems known in the art, the system of the present disclosure may perform inaccurately for poor quality pulse signals because the prior information provides no useful information in such a case. FIG. 10 illustrates such a scenario wherein HR monitoring is inaccurately performed by an embodiment of the system of the present disclosure.

Thus, in accordance with the present disclosure, systems and methods of the present disclosure use face videos acquired from a low cost camera in contact-less manner. HR monitoring using face videos has found limited applicability because the monitoring is prone to error due to respiration, facial expressions, out-of-plane movements, camera parameters and environmental factors. For better HR monitoring, systems and methods of the present disclosure use filtering, modelling and HR tracking. Fourier basis function based modelling handles the out-of-plane movements. It reconstructs the poor quality pulse signal estimates using the good quality pulse signal estimates. The quality parameter has been defined according to the out-of-plane movements. The noise can result in spurious HR thus a Bayesian decision theory based mechanism has been proposed which performs HR tracking using previous HR estimates and quality estimate for better HR monitoring.

Experimental results have demonstrated that HR monitoring can be significantly improved when both pulse modelling and HR tracking are incorporated. Further, it has performed in near real-time and offered good HR monitoring with an average absolute error of 1.329 bpm and the Pearson correlation between predicted and actual heart rate is 0.975. This indicates that the proposed system can be effectively used for HR monitoring.

The written description describes the subject matter herein to enable any person skilled in the art to make and use the embodiments of the present disclosure. The scope of the subject matter embodiments defined here may include other modifications that occur to those skilled in the art. Such other modifications are intended to be within the scope if they have similar elements that do not differ from the literal language of the claims or if they include equivalent elements with insubstantial differences from the literal language.

The scope of the subject matter embodiments defined here may include other modifications that occur to those skilled in the art. Such other modifications are intended to be within the scope if they have similar elements that do not differ from the literal language of the claims or if they include equivalent elements with insubstantial differences from the literal language.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments of the present disclosure may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules comprising the system of the present disclosure and described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device. The various modules described herein may be implemented as software and/or hardware modules and may be stored in any type of non-transitory computer readable medium or other storage device. Some non-limiting examples of non-transitory computer-readable media include CDs, DVDs, BLU-RAY, flash memory, and hard disk drives.

Further, although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

It is intended that the disclosure and examples be considered as exemplary only, with a true scope and spirit of disclosed embodiments being indicated by the following claims.

What is claimed is:
1. A processor implemented method (200) comprising:
extracting in real time a plurality of non-overlapping windows from an input video with a detected face, wherein the non-overlapping windows correspond to time intervals of the input video, each of the time intervals containing an equal number of frames (202);
analyzing each of the non-overlapping windows (204) by:
extracting a pulse signal from each of the non-overlapping windows (204a);

estimating a first quality measure as a quality of the pulse signal in each of the frames based on out-of-plane movement in a z direction, wherein the first quality measure has (f−1) values for f number of the frames (204b);

estimating a second quality measure based on peak signal to noise ratio (PSNR), wherein the second quality measure is a single value for the pulse signal (204c); and post processing the pulse signal, to obtain a modelled pulse signal from each of the overlapping windows, by reconstructing the pulse signal at the frames affected by the out-of-plane movements using the remaining frames (204d); and tracking heart rate corresponding to the modelled pulse signal based on a Bayesian decision theory (206), wherein tracking the heart rate comprises:

estimating the heart rate using the Bayesian decision theory by estimating a current heart rate corresponding to a current modelled pulse signal using previous heart rate of a preceding modelled pulse signal and the second quality measure associated with the current and the preceding modelled pulse signals; and analyzing a spectrum associated with the modelled pulse signal from each of the non-overlapping windows to identify frequency of a maximum amplitude corresponding to the heart rate thereof as an HR frequency; and wherein using the Bayesian decision theory comprises:

determining a quality of the previous heart rate estimate by utilizing the second quality measure;

calculating a Gaussian distribution of a prior information pertaining to a previously tracked HR and a likelihood function of a current modelled pulse signal by defining a measure of confidence in the previous heart rate estimate along with the determined quality of the previous heart rate estimate;

estimating the prior information required for current heart rate estimation, wherein the prior information is estimated by finding a normalized sum of the Gaussian distribution of the prior information and a parameter θ defined in the HR frequency ranges of 0.7 Hz to 4 Hz;

estimating the likelihood function for determining the current heart rate estimate, wherein the likelihood function is estimated by normalizing the spectrum of the modelled pulse signal corresponding to a current window;

estimating the posterior probability of heart rate frequency by applying Bayes rule, wherein the posterior probability is estimated based on the prior information and the likelihood function; and estimating a current heart rate frequency, wherein the current heart rate frequency corresponds to the value at which posterior probability is maximum.

2. The processor implemented method of claim 1, wherein the step of extracting a pulse signal comprises:

identifying a Region of Interest (ROI) corresponding to the detected face in each of the non-overlapping windows, wherein a face area associated with the detected face is divided into non-overlapping square blocks;

performing frame registration between a previous frame and a current frame within each of the non-overlapping windows based on a pre-defined subset of facial landmark points to stabilize location of the ROI in presence of in-plane movement;

extracting temporal signals from each of the non-overlapping square blocks of the ROI using Eulerian method, wherein the temporal signals correspond to motion or color variations in the detected face across time; and estimating the pulse signal from the extracted temporal signals using a kurtosis based optimization method.

3. The processor implemented method of claim 1, wherein the step of estimating a first quality measure as a quality of the pulse signal in each of the frames based on out-of-plane movement in a z direction comprises:

calculating a deviation introduced by a change of location of pre-defined facial landmark points in the z direction, wherein the deviation is calculated between each pair of consecutive frames in each of the non-overlapping windows;

estimating the first quality measure by utilizing the pre-defined facial landmark points having a largest deviation in the z direction by:

normalizing the deviations in the pre-defined facial landmark points in the z direction to [0,1]; and estimating the first quality measure by subtracting the normalized deviations from 1 such that low and high deviations result in high and low values for the first quality measure respectively as $$\hat{q}_{(k-1)} = 1 - \left( \frac{d_{(k-1)} - \min(d)}{\max(d) - \min(d)} \right).$$

4. The processor implemented method of claim 1, wherein the post processing of the pulse signal comprises reconstructing the pulse signals at the frames affected by the out-of-plane movements using Fourier basis function based pulse signal modelling, the pulse signal modelling comprising:

decomposing the pulse signal at the frames affected by the out-of-plane movements using the Fourier basis function;

estimating pulse signal modelling parameters by using a weighted least square equation, wherein the pulse signal modelling parameters represent a contribution of the Fourier basis function and weights refer to the first quality measure, wherein solving the weighted least square equation is based on a pseudo inverse equation for minimizing an associated weighted error, and wherein the weighted error is based on the first quality measure and a reconstruction error at each frame; and obtaining the modelled pulse signal based on the estimated modelling parameters and the Fourier basis function.

5. A system (100) comprising:

one or more processors (104); and one or more internal data storage devices (102) operatively coupled to the one or more processors (104) for storing instructions configured for execution by the one or more processors to:

extract in real time a plurality of non-overlapping windows from an input video with a detected face, wherein the non-overlapping windows correspond to time intervals of the input video, each of the time intervals containing an equal number of frames;

extract a pulse signal from each of the non-overlapping windows;

estimate a first quality measure as a quality of the pulse signal in each of the frames based on out-of-plane movement in a z direction, wherein the first quality measure has (f−1) values for f number of the frames;

estimate a second quality measure based on peak signal to noise ratio (PSNR), wherein the second quality measure is a single value for the pulse signal; and post process the pulse signal by reconstructing the pulse signal at the frames affected by the out-of-plane movements using the remaining frames to obtain modelled pulse signals; and track heart rate corresponding to the modelled pulse signal from each of the non-overlapping windows based on a Bayesian decision theory, wherein the heart rate is tracked by:

estimating the heart rate using the Bayesian decision theory by estimating a current heart rate corresponding to a current modelled pulse signal using previous heart rate of a preceding modelled pulse signal and the second quality measure associated with the current and the preceding modelled pulse signals; and analyzing a spectrum associated with the modelled pulse signal from each of the non-overlapping windows to identify frequency of a maximum amplitude corresponding to the heart rate thereof as an HR frequency; and wherein using the Bayesian decision theory comprises:

determining a quality of the previous heart rate estimate by utilizing the second quality measure;

calculating a Gaussian distribution of a prior information pertaining to a previously tracked HR and a likelihood function of a current modelled pulse signal by defining a measure of confidence in the previous heart rate estimate along with the determined quality of the previous heart rate estimate;

estimating the prior information required for current heart rate estimation, wherein the prior information is estimated by finding a normalized sum of the Gaussian distribution of the prior information and a parameter θ defined in the HR frequency ranges of 0.7 Hz to 4 Hz;

estimating the likelihood function for determining the current heart rate estimate, wherein the likelihood function is estimated by normalizing the spectrum of the modelled pulse signal corresponding to a current window;

estimating the posterior probability of heart rate frequency by applying Bayes rule, wherein the posterior probability is estimated based on the prior information and the likelihood function; and estimating a current heart rate frequency, wherein the current heart rate frequency corresponds to the value at which posterior probability is maximum.

6. The system of claim 5, wherein the one or more processors are is further configured to extract the pulse signal by:

identifying a Region of Interest (ROI) corresponding to the detected face in each of the non-overlapping windows, wherein a face area associated with the detected face is divided into non-overlapping square blocks;

performing frame registration between a previous frame and a current frame within each of the non-overlapping windows based on a pre-defined subset of facial landmark points to stabilize location of the ROI in presence of in-plane movement;

extracting temporal signals from each of the non-overlapping square blocks of the ROI using Eulerian method, wherein the temporal signals correspond to motion or color variations in the detected face across time; and estimating the pulse signal from the extracted temporal signals using a kurtosis based optimization method.

7. The system of claim 5, wherein the one or more processors are further configured to estimate a first quality measure as a quality of the pulse signal in each of the frames based on out-of-plane movement in a z direction by:

calculating a deviation introduced by a change of location of pre-defined facial landmark points in the z direction, wherein the deviation is calculated between each pair of consecutive frames in each of the non-overlapping windows;

estimating the first quality measure by utilizing the pre-defined facial landmark points having a largest deviation in the z direction by:

normalizing the deviations in the pre-defined facial landmark points in the z direction to [0,1]; and estimating the first quality measure by subtracting the normalized deviations from 1 such that low and high deviations result in high and low values for the first quality measure respectively as $$\hat{q}_{(k-1)} = 1 - \left(\frac{d_{(k-1)} - \min(d)}{\max(d) - \min(d)}\right).$$

8. The system of claim 5, wherein the one or more processors are further configured to post process the pulse signal by reconstructing the pulse signals at the frames affected by the out-of-plane movements using Fourier basis function based pulse signal modelling, wherein the pulse signal modelling comprises:

decomposing the pulse signal at the frames affected by the out-of-plane movements using the Fourier basis function;

estimating pulse signal modelling parameters by using a weighted least square equation, wherein the pulse signal modelling parameters represent a contribution of the Fourier basis function and weights refer to the first quality measure, wherein solving the weighted least square equation is based on a pseudo inverse equation for minimizing an associated weighted error, and wherein the weighted error is based on the first quality measure and a reconstruction error at each frame; and obtaining the modelled pulse signal based on the estimated modelling parameters and the Fourier basis function.

9. A computer program product comprising a non-transitory computer readable medium having a computer readable program embodied therein, wherein the computer readable program, when executed on a computing device, causes the computing device to:

extract in real time a plurality of non-overlapping windows from an input video with a detected face, wherein the non-overlapping windows correspond to time intervals of the input video, each of the time intervals containing an equal number of frames;

analyze each of the non-overlapping windows by:
  extracting a pulse signal from each of the non-overlapping windows;
  estimating a first quality measure as a quality of the pulse signal in each of the frames based on out-of-plane movement in a z direction, wherein the first quality measure has (f−1) values for f number of the frames;
  estimating a second quality measure based on peak signal to noise ratio (PSNR), wherein the second quality measure is a single value for the pulse signal; and
  post processing the pulse signal, to obtain a modelled pulse signal from each of the overlapping windows, by reconstructing the pulse signal at the frames affected by the out-of-plane movements using the remaining frames; and
    track heart rate corresponding to the modelled pulse signal based on a Bayesian decision theory, wherein the heart rate is tracked by:
      estimating the heart rate using the Bayesian decision theory by estimating a current heart rate corresponding to a current modelled pulse signal using previous heart rate of a preceding modelled pulse signal and the second quality measure associated with the current and the preceding modelled pulse signals; and
      analyzing a spectrum associated with the modelled pulse signal from each of the non-overlapping windows to identify frequency of a maximum amplitude corresponding to the heart rate thereof as an HR frequency; and wherein using the Bayesian decision theory comprises:
        determining a quality of the previous heart rate estimate by utilizing the second quality measure;
        calculating a Gaussian distribution of a prior information pertaining to a previously tracked HR and a likelihood function of a current modelled pulse signal by defining a measure of confidence in the previous heart rate estimate along with the determined quality of the previous heart rate estimate;
        estimating the prior information required for current heart rate estimation, wherein the prior information is estimated by finding a normalized sum of the Gaussian distribution of the prior information and a parameter $\theta$ defined in the HR frequency ranges of 0.7 Hz to 4 Hz;
        estimating the likelihood function for determining the current heart rate estimate, wherein the likelihood function is estimated by normalizing the spectrum of the modelled pulse signal corresponding to a current window;
        estimating the posterior probability of heart rate frequency by applying Bayes rule, wherein the posterior probability is estimated based on the prior information and the likelihood function; and
        estimating a current heart rate frequency, wherein the current heart rate frequency corresponds to the value at which posterior probability is maximum.

* * * * *